US007973176B2

(12) United States Patent
Takeda et al.

(10) Patent No.: US 7,973,176 B2
(45) Date of Patent: Jul. 5, 2011

(54) PROCESS FOR PRODUCTION OF ARALKYLOXYPYRROLIDINE DERIVATIVE

(75) Inventors: Toshihiro Takeda, Takasago (JP); Masatoshi Ohnuki, Takasago (JP); Narumi Kishimoto, Takasago (JP)

(73) Assignee: Kaneka Corporation, Osaka (JP)

( * ) Notice: Subject to any disclaimer, the term of this patent is extended or adjusted under 35 U.S.C. 154(b) by 406 days.

(21) Appl. No.: 11/990,766

(22) PCT Filed: Aug. 22, 2006

(86) PCT No.: PCT/JP2006/316435
§ 371 (c)(1),
(2), (4) Date: Feb. 21, 2008

(87) PCT Pub. No.: WO2007/023824
PCT Pub. Date: Mar. 1, 2007

(65) Prior Publication Data
US 2008/0306283 A1   Dec. 11, 2008

(30) Foreign Application Priority Data
Aug. 23, 2005 (JP) .................... 2005-241742

(51) Int. Cl.
*C07D 207/12* (2006.01)
(52) U.S. Cl. ........................................ 548/541
(58) Field of Classification Search ............... 548/541
See application file for complete search history.

(56) References Cited

U.S. PATENT DOCUMENTS

| 5,037,841 A * | 8/1991 | Schohe et al. ............ 514/373 |
| 5,854,268 A | 12/1998 | Baker et al. |
| 7,268,236 B2 | 9/2007 | Kano et al. |

FOREIGN PATENT DOCUMENTS

| JP | 1-311059 | 12/1989 |
| WO | 96/04274 | 2/1996 |
| WO | 03/082815 | 10/2003 |
| WO | WO 2004099137 A1 * | 11/2004 |

OTHER PUBLICATIONS

Pavia et al., Introduction to Organic Laboratory Techniques—A Microscale Approach 1990, Technique 5 on pp. 577-596.*
N.G. Anderson, Practical Process Research & Development 2000, Chapter 10, pp. 203-221.*
Extended European Search Report issued for the counterpart European Patent Application No. 06 79 6649 on Apr. 24, 2009.
International Search Report issued Nov. 21, 2006 in the International (PCT) Application PCT/JP2006/316435 of which the present application is the U.S. National Stage.
International Preliminary Report on Patentability issued Mar. 6, 2008 in the International (PCT) Application PCT/JP2006/316435 of which the present application is the U.S. National Stage together with translation of PCT Written Opinion issued for the International Application.
Francine Sternfeld et al., "Synthesis and Serotonergic Activity of 3-[2-(Pyrrolidin-1-yl)ethyl]indoles: Potent Agonists for the h5-$HT_{1D}$ Receptor with High Selectivity over the h5-$HT_{1B}$ Receptor", Journal of Medicinal Chemistry, vol. 42, No. 4, pp. 677-690, 1999.
Zhenliang Chen et al., "Cumyl: A Better N-Protecting Group of α-Diazo Acetamides for Intramolecular C-H Insertion Reaction and its Application in the Synthesis of Pregabalin and 3-Benzyloxy Pyrrolidine", Synlett, No. 10, pp. 1763-1764, 2004.
Shigeru Arai et al., "Phase-transfer-catalyzed asymmetric Michael reaction using newly-prepared chiral quaternary ammonium salts derived from L-tartrate", Tetrahedron Letters, vol. 43, No. 52, pp. 9535-9537, 2002.
Dominique Potin et al., "De novo design, synthesis, and in vitro activity of LFA-1 antagonists based on a bicyclic[5.5]hydantoin scaffold", Bioorganic & Medicinal Chemistry Letters, vol. 15, No. 4, pp. 1161-1164, 2005.
Armen M. Boldi et al., "Solid-Phase Library Synthesis of Alkoxyprolines", Journal of Combinatorial Chemistry, vol. 3, No. 4, pp. 367-373, 2001.
Frank Schieweck et al., "Synthesis of geminal bis(hydroxymethyl)pyrrolidine and pyrrolizidine imino sugars", Journal of the Chemical Society, Perkin Transactions, vol. 24, pp. 3409-3414, 2001.
Notice of Reasons for Refusal, and English translation thereof, issued Apr. 22, 2008 in connection with Japanese Patent Application No. JP2007-532139.
Shadan Houjin Nihon Kagakukai Hen (The Chemical Society of Japan ed.), "4.3.1a., Saikessho (Recrystallization)", Jikken Kagaku Kouza 1 (Experimental Chemical Course 1), vol. 4, pp. 184-186, 1990 along with English translation thereof.

* cited by examiner

*Primary Examiner* — Jason M Nolan
(74) *Attorney, Agent, or Firm* — Wenderoth, Lind & Ponack, L.L.P.

(57) ABSTRACT

The present invention provides a process for producing a 3-aralkyloxypyrrolidine derivative which is important for production of pharmaceutical products and the like. In the present invention, a N-protected-3-hydroxypyrrolidine is converted into a N-protected-3-aralkyloxypyrrolidine by allowing an aralkyl halide to act in the presence of a base and at least one of a metal halide and a phase-transfer catalyst followed by deprotecting a N-protecting group to convert it to a 3-aralkyloxypyrrolidine derivative and subsequently treating the derivative in a solvent containing a polar solvent, thereby obtaining the 3-aralkyloxypyrrolidine derivative as a crystal. According to the present invention, a 3-aralkyloxypyrrolidine derivative of high purity can be produced conveniently and efficiently on an industrial scale.

10 Claims, No Drawings

PROCESS FOR PRODUCTION OF ARALKYLOXYPYRROLIDINE DERIVATIVE

FIELD OF THE INVENTION

The present invention relates to a process for producing a 3-aralkyloxypyrrolidine derivative represented by a following general formula (2):

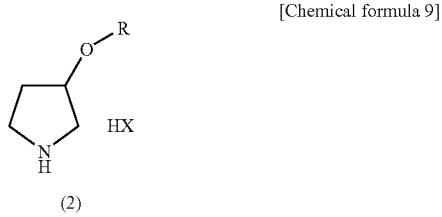

[Chemical formula 9]

(2)

wherein R represents an aralkyl group having 7 to 15 carbon atoms which may have a substituent; and HX represents a mineral acid, a sulfonic acid, a carboxylic acid, and an amino acid. In particular, (R)-3-benzyloxypyrrolidine, or its salt with an acid is known as a compound which is useful as a production intermediate product such as a pharmaceutical product and the like.

BACKGROUND ART

As a process for producing a 3-aralkyloxypyrrolidine derivative (2), following methods are conventionally used.
(i) After 4M hydrogen chloride in anhydrous dioxane is added to N-Boc-3-benzyloxypyrrolidine at 0° C., the mixture is concentrated, and dissolved in toluene. After stirring, syrupy 3-benzyloxypyrrolidine is obtained (for example, refer to Patent document 1).
(ii) 4-benzyloxypyrrolidine-2-on is reduced with LiAlH$_4$ to obtain 3-benzyloxypyrrolidine (for example, refer to Nonpatent literature 1).
(iii) (R)—N-Boc-3-benzyloxypyrrolidine is stirred in 90% aqueous solution of formic acid at from 0° C. to room temperature and the solvent is distilled away under reduced pressure, and then the resultant residue is neutralized with an aqueous solution of K$_2$CO$_3$. After the aqueous solution is extracted with n-butanol, the solvent is removed under reduced pressure and then treated by silica gel column chromatography, thereby obtaining (R)-3-benzyloxypyrrolidine (for example, refer to Patent document 2 and Nonpatent literature 2).

However, as described in the method (i), since a 3-aralkyloxypyrrolidine derivative (2) such as 3-benzyloxypyrrolidine hydrochloride is not suitable in terms of affinity with various solvents, particularly nonpolar solvents such as hydrocarbon solvents, the 3-aralkyloxypyrrolidine derivative (2) turns into oil form in a solvent comprising these solvents as a main solvent, so that a suitable crystallization thereof is difficult. Additionally, properties of the substance such as moisture absorption property are not known almost at all, and there has been no disclosure as to problems in treating the substance on an industrial scale and solutions for the problems.

With respect to (ii), since LiAlH$_4$ is used as a reaction reagent, the method has a danger of generating hydrogen at a time of reaction and requires troublesome treatments in disposing aluminum generated as by-product after the reaction, and there is a substantial problem in production on a commercial scale. Additionally, in a case where 4-benzyloxypyrrolidine-2-on is reduced by the method, since resultant 3-hydroxypyrrolidine is a racemate, it is not a suitable method when a desired substance is optically active 3-aralkyloxypyrrolidine.

With respect to a purification method of 3-aralkyloxypyrrolidine, a purification method by column chromatography according to the method (iii) is disclosed, but there are problems in production on a commercial scale such as unfavorable heavy consumption of solvents, complexity of processes and an accompanying waste of time, increase in the number and capacity of production apparatus, and decrease in yield.

As described above, with respect to the 3-aralkyloxypyrrolidine derivative (2) such as 3-benzyloxypyrrolidine, there is no disclosure of a crystallization method thereof, an industrially efficient purification method, and a method for handling thereof, so that there is a demand for developing a method of industrially and conveniently crystallizing the compound and a purification method for obtaining the compound with high purity, and a suitable method for handling on an industrial scale.

Further, with respect to a process for producing N-protected-3-aralkyloxypyrrolidine (1) which is a raw material of the present invention, there is known a method converting from a N-protected-3-hydroxypyrrolidine (5); for example, a method allowing benzyl bromide to act in the presence of NaH (for example, Nonpatent literature 2) in an organic solvent is known; the N-protected-3-aralkyloxypyrrolidine (1) and the N-protected-3-hydroxypyrrolidine (5) are represented by:

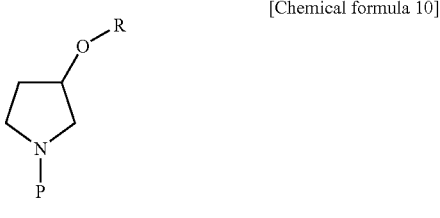

[Chemical formula 10]

(1)

wherein P represents a protecting group of an amino group; and R represents the same as above; and

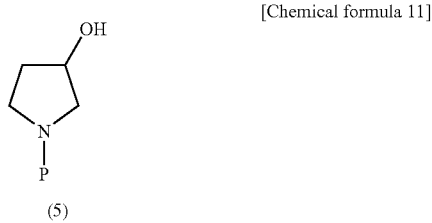

[Chemical formula 11]

(5)

wherein P represents a protecting group of an amino group. However, in the above method, NaH has dangers of hydrogen generation and ignition by contact with moisture, and benzyl bromide is substantially difficult to obtain on an industrial scale due to having a strong tearing property. Therefore, the above method is not necessarily a suitable process for producing N-protected-3-aralkyloxypyrrolidine industrially.
[Patent document 1] Japanese unexamined patent publication No. 1-311059
[Patent document 2] WO9604274
[Nonpatent literature 1] Synlett 2004, No. 10, 1763-1764
[Nonpatent literature 2] J. Med. Chem., 1999, 42, 677-690

DISCLOSURE OF THE INVENTION

Problem to be Solved by the Invention

In view of the above problems, an object of the present invention is to provide a process for producing a 3-aralkyloxypyrrolidine derivative (2) such as 3-benzyloxypyrrolidine with high purity conveniently and efficiently and with extremely high productivity on an industrial scale. It is also an object of the present invention to provide a suitable method for handling of a 3-aralkyloxypyrrolidine derivative (2) on an industrial scale. Further, it is also an object of the present invention to provide a N-protected-3-aralkyloxypyrrolidine (1) which is a raw material conveniently and safely on an industrial scale.

Means for Solving Problem

The present inventors, as the result of an intensive examination to solve the above problems, found that a 3-aralkyloxypyrrolidine derivative (2) can be crystallized by using a solvent comprising a polar organic solvent as a crystallization solvent, thereby producing a 3-aralkyloxypyrrolidine derivative (2) with high purity.

The present inventors also found that a chemical purity can be improved by a series of operations of treating an aqueous layer with a base after removing an organic layer from a two-phase mixture of water and an organic solvent comprising a 3-aralkyloxypyrrolidine derivative (2), extracting a free amine of a 3-aralkyloxypyrrolidine derivative (2) using an organic solvent, and treating the free amine with an acid to convert to the 3-aralkyloxypyrrolidine derivative (2).

Further, the present inventors found that a N-protected-3-aralkyloxypyrrolidine can be produced safely and conveniently by O-aralkylation of a N-protected-3-hydroxypyrrolidine (5) by allowing an aralkyl halide to act in the presence of a base and at least one of a metal halide and a phase-transfer catalyst.

Further, the present inventors found that, with respect to a crystal of a 3-aralkyloxypyrrolidine hydrohalide (3), since an equilibrium moisture content thereof (in other words, absorption of moisture behavior) changes considerably on reaching an absolute humidity of about 12 $g/m^3$ absorption of moisture of the crystal of the 3-aralkyloxypyrrolidine hydrohalide (3) can be suitably suppressed by controlling surrounding environment during treatment at an absolute humidity of about 12 $g/m^3$ or less, so that problems such as deliquescence can be solved.

The present invention is completed based on the series of findings above. Namely, the present invention relates to a process for producing a 3-aralkyloxypyrrolidine derivative (2) characterized by subjecting a 3-aralkyloxypyrrolidine derivative represented by the above formula (2) to a crystallization process using a solvent comprising a polar organic solvent to obtain it as a crystal.

The present invention relates to a process for producing a 3-aralkyloxypyrrolidine derivative characterized by improving a chemical purity by a series of operations of:
A) treating an aqueous layer with a base after removing an organic layer from a two-phase mixture of water and an organic solvent containing a 3-aralkyloxypyrrolidine derivative represented by the above formula (2);
B) extracting a free amine of the 3-aralkyloxypyrrolidine derivative (2) using an organic solvent; and
C) treating the free amine with an acid to convert to the 3-aralkyloxypyrrolidine derivative (2).

Additionally, the present invention relates to a process for producing N-protected-3-aralkyloxypyrrolidine represented by the above formula (1) characterized by O-aralkylation of a N-protected-3-hydroxypyrrolidine represented by the above formula (5) by allowing aralkyl halide to act in the presence of a base and at least one of a metal halide and a phase-transfer catalyst.

Additionally, the present invention relates to a crystal of a 3-benzyloxypyrrolidine derivative represented by the following general formula (4):

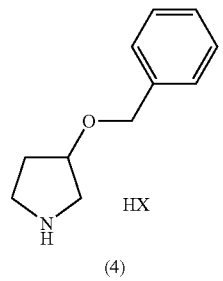

[Chemical formula 12]

(4)

wherein HX represents a mineral acid, sulfonic acid, carboxylic acid or amino acid.

Additionally, the present invention relates to a method for handling a 3-aralkyloxypyrrolidine hydrohalide characterized by handling a crystal of a 3-aralkyloxypyrrolidine hydrohalide under an environment of absolute humidity of 12 $g/m^3$ or less; and the 3-aralkyloxypyrrolidine hydrohalide is represented by a general formula (3):

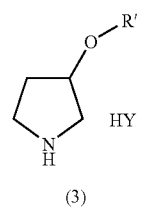

[Chemical formula 13]

(3)

wherein R' represents an aralkyl group having 7 to 15 carbon atoms which may have a substituent, HY represents hydrogen halide.

EFFECT OF THE INVENTION

According to the present invention, a 3-aralkyloxypyrrolidine derivative (2) can be produced conveniently and efficiently with extremely high productivity on a commercial scale. Additionally, a crystal of a 3-aralkyloxypyrrolidine hydrohalide (3) can be handled stably on an industrial scale. Further, a N-protected-3-aralkyloxypyrrolidine (1) which is a raw material can be efficiently and safely produced on an industrial scale.

DESCRIPTION OF THE PREFERRED EMBODIMENT

The present invention comprises following steps.

[Chemical formula 14]

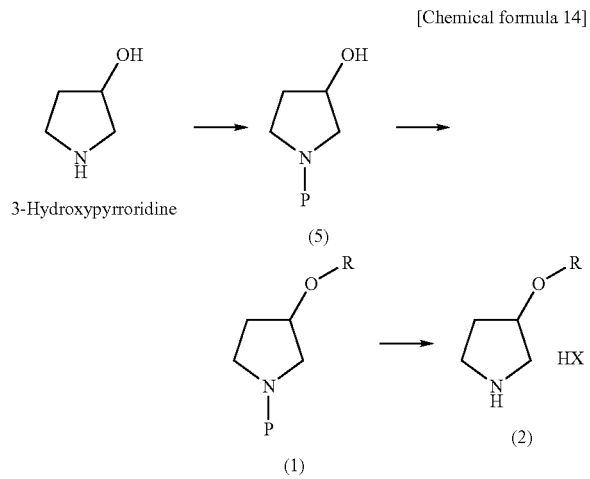

Hereinafter, each step of the present invention is explained in detail.

First, a step of converting 3-hydroxypyrrolidine into N-protected-3-hydroxypyrrolidine represented by a general formula (5) is explained:

[Chemical formula 15]

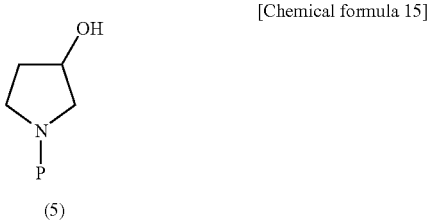

In the above formula (5), P represents a protecting group of amino group. The protecting group of amino group is a group which protects an amino group, and groups which can be commonly used are described in PROTECTIVE GROUPS IN ORGANIC SYNTHESIS 2nd. Ed., published by JOHN WILEY&SONS (1991). In the above formula (1), preferred as the protecting group are urethane-type protecting groups (also referred to as carbamate-type protecting groups). Among them, preferred is a lower alkoxycarbonyl group (an alkyl group of which has 1 to 6 carbon atoms, preferably 1 to 4 carbon atoms), more preferably a methoxycarbonyl group, an ethoxycarbonyl group, or a tert-butoxycarbonyl group, and the tert-butoxycarbonyl group is particularly preferred.

The reaction can be carried out by a publicly known method described in the technical book. The method is not particularly limited, and for example, a carbamate-type protecting group can be introduced onto an amino group by treating 3-hydroxypyrrolidine with di-tert-butoxy dicarbonate.

The 3-hydroxypyrrolidine to be used may be an optical active compound or a non-optical active compound.

Next, a step of O-aralkylation of N-protected-3-hydroxypyrrolidine (5) followed by conversion to N-protected-3-aralkyloxypyrrolidine represented by general formula (1) is explained:

[Chemical formula 16]

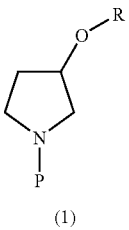

O-aralkylation means converting a hydroxy group to an aralkyloxy group. Group R which is bonded to a hydroxyl group at 3-position in the above formula (1) is an aralkyl group having 7 to 15 carbon atoms which may have a substituent. Examples of the substituent include a hydroxyl group, a halogen atom, an amino group, a nitro group, and an alkoxy group. Examples of the aralkyl group having 7 to 15 carbon atoms which may have a substituent include a benzyl group, a p-chlorobenzyl group, a p-hydroxybenzyl group, a p-fluorobenzyl group, a m,m-difluorobenzyl group, a phenylethyl group, a naphthylmethyl group and the like. It is preferably an aralkyl group having 7 or 8 carbon atoms which may have a substituent, even more preferably a benzyl group which may have a substituent, particularly preferably a benzyl group.

A N-protected-3-hydroxypyrrolidine (5) used in the present step may be one synthesized by the above process, or may be one separately synthesized by a publicly known method.

The N-protected-3-aralkyloxypyrrolidine (1) may be an optical active compound or a non-optical active compound.

A reaction of the process is preferably carried out in the presence of a base and at least one of a metal halide and a phase-transfer catalyst.

As the above base, either an inorganic base or an organic base may be used, but it is preferably the inorganic base, and specifically include, although not particularly limited, an alkali metal hydroxide such as sodium hydroxide and potassium hydroxide; an alkali metal carbonate such as sodium carbonate and potassium carbonate; and an alkali metal hydrogen carbonate such as sodium hydrogen carbonate. Among them, the alkali met-al hydroxide is preferred.

An amount of the base to be used is not particularly limited, and normally it is from 1 to 30 times mol, preferably from 1 to 20 times mol, more preferably 2 to 10 times mol, particularly preferably from 2 to 5 times mol with respect to the N-protected-3-hydroxypyrrolidine (5).

The metal halide is not particularly limited, and includes an alkali metal halide such as lithium bromide, sodium bromide, potassium bromide, lithium iodide, sodium iodide and potassium iodide; an alkaline-earth metal halide such as magnesium bromide, calcium bromide, magnesium iodide, and calcium iodide; and an aluminum halide such as aluminum bromide and aluminum iodide, and it is preferably an alkali metal halide, even more preferably potassium iodide.

An amount of alkali metal halide to be used is not particularly limited, and in general, it is preferably from 0.01 to 5 mol %, more preferably from 0.05 mol to 1 mol % with respect to the N-protected-3-hydroxypyrrolidine (5).

The phase-transfer catalyst is not particularly limited, and such examples include a crown ether such as 12-crown-4,15-crown-5,18-crown-6,24-crown-8, dibenzo-18-crown-6, dibenzo-24-crown-8, dicyclohexyl-18-crown-6, and dicyclohexyl-24-crown-8; a cryptand such as cryptand [2,2], cryptand [2,2,1], and cryptand [2,2,2]; and a quaternary ammonium salt such as trioctylmethylammonium chloride [commercial name: ALIQUAT 336], trioctylmethylammonium bromide, methyltrialkyl (having 8 to 10 carbon atoms) ammonium chloride [commercial name: Adogen 464], tetrabutylammonium chloride, tetrabutylammonium bromide, and tetrabutylammonium iodide. Among the above phase-transfer catalysts, in general, a quaternary ammonium salt is preferred, and among them, tetrabutylammonium bromide is preferably used.

An amount of the phase-transfer catalyst to be used is not particularly limited, and in general, it is preferably from 0.01 to 5 mol %, more preferably from 0.05 mol to 1 mol % with respect to the N-protected-3-hydroxypyrrolidine (5).

The reaction of the step can be carried out in the presence of a base and a metal halide (embodiment a); in the presence of a base and a phase-transfer catalyst (embodiment b); or in the presence of a base, a metal halide and a phase-transfer catalyst (embodiment c). Embodiment a or embodiment c is preferable, and embodiment a where the reaction is carried out in the presence of a base and a metal halide is more preferable.

A reaction solvent is not particularly limited as long as it is essentially inactive, and for example, a hydrocarbon solvent, an ether solvent, a nitrogen-containing solvent, or a sulfur-containing solvent are preferably used in order to reduce a residual of the N-3-hydroxypyrrolidine (5).

The hydrocarbon solvent is not particularly limited, and such examples include an aromatic hydrocarbon such as benzene, toluene, xylene, chlorobenzene, and chlorotoluene; and an aliphatic hydrocarbon such as cyclohexane, methylcyclohexane, and heptane, but it is preferably an aromatic hydrocarbon, even more preferably toluene.

The ether solvent is not particularly limited, and specifically, such examples include tetrahydrofuran, 1,4-dioxane, dimethoxyethane, ethylene glycol dimethyl ether and the like, and it is preferably 1,4-dioxane.

Specifically, the nitrogen-containing solvent include, for example, a nitrogen-containing compound such as acetonitrile, dimethylformamide, dimethylacetamide, diethylacetamide, dimethylbutylamide, N-methyl-2-pyrrolidone, hexamethylphosphoric triamide and the like, but are not limited to these. It is preferably acetonitrile.

The sulfur-containing solvent is not particularly limited, and such example include dimethyl sulfoxide and the like.

An amount of the organic solvent to be used is not particularly limited, and a lower limit thereof is normally 10 wt %, preferably 50 wt %, more preferably 100 wt % with respect to N-protected-3 hydroxypyrrolidine (5). an upper limit is not particularly limited, and considering economic efficiency, it is normally 10000 wt %, preferably 5000 wt %, more preferably 2000 wt %.

As a reaction solvent used in O-aralkylation reaction of the present invention, the above solvents may be used alone or two or more kinds of the above solvents are combined. Alternatively, water may also be contained as necessary.

The reaction of the step may be carried out using aralkyl halide. The aralkyl group of the aralkyl halide is same as the aralkyl group explained as R in the above formula (1). The halogen of the aralkyl halide is not particularly limited, and is preferably chlorine, bromine or iodine, more preferably chlorine or iodine, particularly preferably chlorine. As the aralkyl halide, benzyl halide is preferred, and benzyl chloride is particularly preferred.

A lower limit of the reaction temperature is not particularly limited as long as it is not less than the freezing point of the reaction solvent, and in general, it is preferably 0° C. or more, more preferably 20° C. or more, even more preferably 40° C.

or more. An upper limit is not particularly limited as long as it is at a boiling point of the reaction solvent or less, and preferably 120° C. or less, more preferably 100° C. or less, even more preferably 80° C. or less.

A reaction time is not particularly limited, and in general, it is preferably from 1 to 100 hours, more preferably from 5 to 80 hours, even more preferably from 10 to 50 hours.

In the above reaction, in a case where the N-protected-3-hydroxypyrrolidine (5) remains after the reaction finished, there arises a problem that the N-protected-3-hydroxypyrrolidine (5) is deprotected in a next step which is a deprotection step of a N-protecting group and is directly contained as impurities in a 3-aralkyloxypyrrolidine derivative represented by the general formula (2). Accordingly, at the end of the reaction, a residual amount of the N-protected-3-hydroxypyrrolidine (5) is preferably small, and the residual amount is normally 10 wt % or less, more preferably 5 wt % or less, even more preferably 3 wt % or less, particularly preferably 2 wt % or less with respect to the produced N-protected-3-aralkyloxypyrrolidine (1). The reaction is preferably continued until the residual amount of the N-protected-3-hydroxypyrrolidine (5) in the reaction mixture becomes the above-mentioned value with respect to the N-protected-3-aralkyloxypyrrolidine (1).

In order to obtain a product from the reaction mixture, a common post-treatment may be carried out. For example, a reaction mixture can be separated to obtain an organic layer containing the product. The resultant organic layer may be washed with water as necessary, and the N-protected-3-aralkyloxypyrrolidine (1) can be obtained by an operation such as heating under reduced pressure to distil away a reaction solvent and an extraction solvent.

The product thus obtained may be subjected to further purification by a common method such as crystallization purification, fractional distillation, column chromatography and the like as necessary to improve purity.

Next, a step of conversion from a N-protected-3-aralkyloxypyrrolidine (1) to a 3-aralkyloxypyrrolidine derivative (2) represented by a general formula (2) is explained:

[Chemical formula 17]

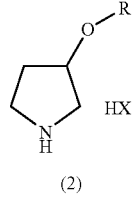

(2)

The 3-aralkyloxypyrrolidine derivative (2) is an acid salt of 3-aralkyloxypyrrolidine. Examples of HX in the above formula (2) include a mineral acid, a sulfonic acid, a carboxylic acid, or an amino acid. These are not limited to a monovalent acid, and may be bivalent or trivalent. The mineral acid is not particularly limited, and includes, for example, a hydrogen halide such as hydrogen chloride and hydrogen bromide; sulfuric acid, phosphoric acid and the like. The sulfonic acid is not particularly limited, and examples include methanesulfonic acid, ethanesulfonic acid, propanesulfonic acid, butanesulfonic acid, benzenesulfonic acid, p-toluenesulfonic acid, camphorsulfonic acid, 1-phenylethanesulfonic acid and the like. The carboxylic acid is not particularly limited, and examples include a non-optically active carboxylic acid such as formic acid, acetic acid, trifluoroacetic acid, benzoic acid, and an optically active carboxylic acid such as tartaric acid.

The amino acid is not particularly limited, and examples include an optically active amino acid such as alanine, valine, phenylalanine, asparagic acid and the like.

Among these acids, hydrogen chloride, hydrogen bromide, p-toluenesulfonic acid, and benzoic acid are preferred in that obtained acid salts are easy to crystallize. Among them, hydrogen chloride and hydrogen bromide are preferred and hydrogen chloride is particularly preferred. In a case where the 3-aralkyloxypyrrolidine derivative (2) to be crystallized is an optical active compound and that an optical purity needs to be enhanced, an optically active acid is preferably used. As the optically active acid, an optically active carboxylic acid and an optically active amino acid is preferably used. Among them, optically active tartaric acid and optically active asparagic acid is preferred.

The N-protected-3-aralkyloxypyrrolidine derivative (1) may be one synthesized by the above method, or one synthesized separately by a publicly known method. The N-protected-3-aralkyloxypyrrolidine derivative (1) may contain a N-protected-3-hydroxypyrrolidine (5) and/or an aralkyl alcohol as impurities. The aralkyl alcohol includes an aralkyl alcohol represented by a general formula:

wherein R is one described above; and the aralkyl alcohol (6) is preferably an aralkyl alcohol having 7 or 8 carbon atoms, more preferably benzyl alcohol.

As the N-protected-3-aralkyloxypyrrolidine derivative (1), either an optical active compound or a non-optical active compound may be used, but in a case where the N-protected-3-aralkyloxypyrrolidine (1) is an optical active compound, the resultant 3-aralkyloxypyrrolidine derivative (2) is also an optical active compound, and in a case where the configuration at 3-position of the N-protected-3-aralkyloxypyrrolidine (1) is (3R), that of the 3-aralkyloxypyrrolidine derivative (2) becomes (3R), while in a case where the former is (3S), the latter becomes (3S).

The reaction of the step can be suitably selected in accordance with the type of P indicating a N-protecting group. A method of deprotection includes, for example, one described in PROTECTIVE GROUPS IN ORGANIC SYNTHESIS 2nd. Ed. For example, in a case where P is tert-butoxycarbonyl, above deprotection by an acid may be carried out or a deprotection may be carried out at the same time as an acid salt of N-protected-3-aralkyloxypyrrolidine derivative (1) is formed by a later described operation.

Next, a process for forming the 3-aralkyloxypyrrolidine derivative (2) which is a salt with an acid and derived from 3-aralkyloxypyrrolidine or N-protected-3-aralkyloxypyrrolidine derivative (1) N-protecting group of which can be removed by an acid is explained.

The acid to be used includes acids described as the HX. An amount of the acid to be used is allowable as long as it is a theoretical amount or more. However, a use of it in excess only means that it is uneconomical; thus, it is normally from 1 to 10 mol times, preferably from 1 to 3 mol times, more preferably from 1 to 2 mol times of the N-protected-3-aralkyloxypyrrolidine.

An addition rate of the acid is not particularly limited, and in order to avoid the progress of deprotection of a hydroxyl group at 3-position, a total amount of the acid to be used is preferably added for ⅙ hour or more, more preferably 1 hour or more, even more preferably 3 hours or more, particularly preferably 6 hours or more. an upper limit of the addition time is not particularly limited, and is preferably 24 hours or less preferably 12 hours or less.

The reaction is normally carried out in a solvent. The solvent is not particularly limited, and examples include an organic solvent such as an alcohol solvent, an ether solvent, an ester solvent, an aromatic hydrocarbon solvent or the like.

The alcohol solvent is not particularly limited, and such examples may include methanol, ethanol, n-propanol, isopropanol, n-butanol, sec-butanol, isobutanol, tert-butanol and the like. Among them, isopropanol is preferred.

The ether solvent is not particularly limited, and such examples include tetrahydrofuran, 1,4-dioxane, 1,3-dioxolan, 1,2-dimethoxyethane, diethylene glycol dimethyl ether, methyl tert-butyl ether and the like. Among them, tetrahydrofuran is preferred.

The ester solvent is not particularly limited, and it is preferably an ester having 2 to 8 carbon atoms, more preferably 4 to 6 carbon atoms, and specific examples include ethyl acetate, n-propyl acetate, isopropyl acetate, n-butyl acetate, tert-butyl acetate and the like. Among them, ethyl acetate is preferred.

The aromatic hydrocarbon solvent is not particularly limited, and it is preferably an aromatic hydrocarbon having 6 to 12 carbon atoms, more preferably 6 to 10 carbon atoms, even more preferably 6 to 8 carbon atoms, and specific examples include benzene, toluene, xylene and the like. Among them, an aromatic hydrocarbon having 7 or 8 carbon atoms, specifically, toluene and xylene are particularly preferred, and toluene is most preferably used.

Among the solvents, in view of giving high reactivity and stability in acid, an alcohol solvent is preferred. Among them, isopropanol is preferred.

Needless to say, the reaction solvent may be used alone, and can also be used as a mixture of two or more kinds. Further, in view of further enhancing reactivity, water may be contained together with the organic solvent. An amount of water to be used is not particularly limited, and it is normally from 0.1 to 50 wt %, preferably from 0.5 to 30 wt %, more preferably from 1 to 20 wt % with respect to a total weight of a reaction liquid.

A reaction temperature is not particularly limited, and it is normally from −20 to 100° C., preferably from 0 to 80° C., more preferably from 20 to 50° C. A reaction time is not particularly limited, and it is normally from 1 to 100 hours, preferably from 1 to 48 hours, more preferably from 1 to 24 hours.

Next, a method for improving a chemical purity of a 3-aralkyloxypyrrolidine derivative (2) is explained. The method is characterized by improving the chemical purity by a series of operations of:

A) treating an aqueous layer with a base after removing an organic layer from a two-phase mixture of water and an organic solvent containing a 3-aralkyloxypyrrolidine derivative (2);

B) extracting a free amine of the 3-aralkyloxypyrrolidine derivative (2) using an organic solvent; and C) treating the free amine with an acid to convert the amine to a 3-aralkyloxypyrrolidine derivative (2).

The 3-aralkyloxypyrrolidine derivative (2) may be one synthesized by the above process, or one synthesized by a publicly known method may also be used for the process, too. In a case where the 3-aralkyloxypyrrolidine derivative (2) synthesized by the above process is used, although it is not particularly limited, a reaction mixture of the above process may be used directly.

The 3-aralkyloxypyrrolidine derivative (2) to be used in the process may be a racemate or an optical active (R)- or (S)-3-aralkyloxypyrrolidine derivative. In terms of usefulness as a pharmaceutical intermediate, the optical active 3-aralkyloxypyrrolidine derivative is preferred.

In the process, impurities contained in the 3-aralkyloxypyrrolidine derivative (2) can be removed effectively. Examples of the impurities include 3-hydroxypyrrolidine and/or an aralkyl alcohol (6). The aralkyl alcohol (6) is the same as described above.

Purity of the 3-aralkyloxypyrrolidine derivative (2) used in the process is not particularly limited, and normally, it is preferably 70% or more, more preferably 80% or more, particularly preferably 85% or more.

A two-phase mixture of water and an organic solvent containing the 3-aralkyloxypyrrolidine derivative (2) may be, for example, a mixture prepared by adding water and the organic solvent to the 3-aralkyloxypyrrolidine derivative (2). The organic solvent to be added is not particularly limited, and a solvent having no compatibility with water is preferred, and such examples include toluene, ethyl acetate, methyl tert-butyl ether, methylene chloride and the like. Among them, toluene and ethyl acetate are preferred, and particularly toluene is preferably used. In a case of using a reaction mixture containing the 3-aralkyloxypyrrolidine derivative (2) synthesized by the above method, water and/or the organic solvent may be suitably added.

An amount of water and the organic solvent in the two-phase mixture is not particularly limited. Additionally, the 3-aralkyloxypyrrolidine derivative (2) may be dissolved into the two-phase mixture, or may be partially deposited.

An aqueous solution containing the 3-aralkyloxypyrrolidine derivative (2) which has been transferred to the aqueous layer may be washed with an organic solvent. The organic solvent for washing is not particularly limited, and the one same as the organic solvent added after the end of the above reaction is preferably used.

The 3-aralkyloxypyrrolidine derivative (2) transferred to an aqueous layer can be converted to a free amine of the 3-aralkyloxypyrrolidine derivative (2) by decomposition of the salt using a base. As the base, an inorganic base and/or an organic base may be used. The inorganic base is not particularly limited, and includes, for example, an alkali metal hydroxide such as lithium hydroxide, sodium hydroxide, and potassium hydroxide; an alkali metal carbonate such as sodium carbonate, potassium carbonate, an alkali metal hydrogen carbonate such as sodium hydrogen carbonate and the like, preferably alkali metal hydroxide, particularly preferably sodium hydroxide. The organic base is not particularly limited, and includes, for example, a primary amine such as methyl amine, ethyl amine, propyl amine, and butyl amine; a secondary amine such as dimethyl amine, diethyl amine, dipropyl amine, diisopropyl amine, and dibutyl amine; a tertiary amine such as trimethyl amine, triethyl amine, tripropyl amine, preferably a tertiary amine such as triethyl amine.

The free amine of the 3-aralkyloxypyrrolidine derivative (2) may be the one chemical purity of which is improved by extracting it into an organic solvent and, as necessary, washing with water. The organic solvent to be used is not particularly limited, and a solvent having no compatibility with water is preferred, and such examples include toluene, ethyl acetate, methyl tert-butyl ether, methylene chloride and the like. Among them, toluene and ethyl acetate are preferred, and in particular, toluene is preferably used. An amount to be used is not particularly limited as long as a free amine of the 3-aralkyloxypyrrolidine derivative can be dissolved. The 3-aralkyloxypyrrolidine derivative (2) can be synthesized by treating the free amine of the 3-aralkyloxypyrrolidine derivative (2) thus obtained with an acid.

The acid to be used includes the acids explained as the HX. Among them, preferable acid is hydrogen chloride, hydrogen bromide, p-toluene sulfonate, and benzoic acid; and a salt obtained by the preferable acid is easy to crystallize. It is more preferably hydrogen chloride and hydrogen bromide, particularly preferably hydrogen chloride.

Next, a method of subjecting a 3-aralkyloxypyrrolidine derivative (2) to crystallization process to obtain it as a crystal is explained.

The 3-aralkyloxypyrrolidine derivative (2) to be used in the step may be one produced from the N-protected-3-hydroxypyrrolidine (5) by the above-described method, or one synthesized by a publicly known method. Additionally, it may be one obtained by enhancing chemical purity of the 3-aralkyloxypyrrolidine derivative (2) by the above described method.

The 3-aralkyloxypyrrolidine derivative (2) used in the present process may be a racemate, or an optical active (R)- or (S)-3-aralkyloxypyrrolidine derivative. In view of usefulness as a pharmaceutical intermediate, the optical active 3-aralkyloxypyrrolidine derivative is preferred.

Purity of the 3-aralkyloxypyrrolidine derivative (2) to be used in the step is not particularly limited, and it is preferably 70% or more, more preferably 80% or more, particularly preferably 85% or more.

The impurities contained in the 3-aralkyloxypyrrolidine derivative (2) to be used in the process include, for example, 3-hydroxypyrrolidine produced by deprotecting N-protected-3-hydroxypyrrolidine and/or an aralkyl alcohol (6). An amount of the 3-hydroxypyrrolidine contained in the 3-aralkyloxypyrrolidine derivative (2) is preferably 10 wt % or less, more preferably 5 wt % or less, even more preferably 3 wt % or less, particularly preferably 2 wt % or less with respect to the 3-aralkyloxypyrrolidine derivative (2). An amount of the aralkyl alcohol (6) is preferably 4 wt % or less, more preferably 3 wt % or less, even more preferably 2 wt % or less.

The crystallization method is not particularly limited, and can be performed by, for example, using commonly used crystallization methods such as reaction crystallization, cooling crystallization, concentration crystallization, crystallization method replacing solvent, crystallization method mixing a poor solvent and/or salting out method; these methods may be used alone or in combination. Additionally, reaction crystallization method for obtaining the crystal of the 3-aralkyloxypyrrolidine derivative (2) can be suitably used, wherein a N-protected-3-aralkyloxypyrrolidine (1) or a 3-aralkyloxypyrrolidine is converted to their acid salt in a polar organic solvent. In the crystallization, a seed crystal may also be added as necessary.

The crystallization method can be applied to a solution or an oily concentrate of 3-aralkyloxypyrrolidine. After a 3-aralkyloxypyrrolidine is obtained by the crystallization method, the 3-aralkyloxypyrrolidine may be dissolved to conduct the crystallization method again to enhance purity of the crystal.

The crystallization method is usually carried out in a polar solvent or a mixture solvent of a polar solvent and a nonpolar solvent. When it is carried out in the mixture solvent of the polar solvent and the nonpolar solvent, a ratio of the mixture is not particularly limited, and in the mixture solvent, a preferable ratio of the polar solvent is 5% or more, more preferably 10% or more, even more preferably 30% or more, particularly preferably 50% or more.

The polar solvent is not particularly limited, and includes, for example, water, an ester solvent, an ether solvent, a halogenated hydrocarbon solvent, a nitrogen-containing solvent, an alcohol solvent, a ketone solvent and the like.

The ester solvent is not particularly limited, and it is preferably an ester having 2 to 8 carbon atoms, more preferably 4 to 6 carbon atoms, and specific examples may include ethyl acetate, n-propyl acetate, isopropyl acetate, n-butyl acetate, tert-butyl acetate and the like. Among them, ethyl acetate is preferred.

The ether solvent is not particularly limited, and includes, for example, tetrahydrofuran, 1,3-dioxolan, 1,2-dimethoxyethane, diethylene glycol dimethyl ether, methyl tert-butyl ether and the like. Among them, methyl tert-butyl ether is preferred.

The halogenated hydrocarbon solvent is not particularly limited, and such examples include methylene chloride, chlorobenzene, dichlorobenzene, 1,2-dichloroethane and the like. Among them, chlorobenzene, or dichloroethane is preferred.

The nitrogen-containing solvent is not particularly limited, and examples include acetonitrile, dimethylformamide, dimethylacetamide, diethylacetamide, dimethylbutylamide, N-methyl-2-pyrrolidone and the like. Among them, acetonitrile is preferred.

The alcohol solvent is not particularly limited, and such examples include methanol, ethanol, n-propanol, isopropanol, n-butanol, sec-butanol, isobutanol, tert-butanol and the like. Among them, isopropanol is preferred.

The ketone solvent is not particularly limited, and such examples include acetone, methylethyl ketone and the like. Among them, acetone is preferred.

As the polar solvent, an ester solvent, a halogenated hydrocarbon solvent, a nitrogen-containing solvent, an alcohol solvent, and a ketone solvent are preferred, and an ester solvent or an alcohol solvent is particularly preferred.

These solvents may be used alone or as a mixture of two or more kinds.

An amount of the polar solvent to be used is not particularly limited, and a lower limit thereof is normally 0.01 times by weight, preferably 0.05 times by weight, more preferably 0.1 times by weight, even more preferably 0.5 times by weight, particularly preferably 1 times by weight, and an upper limit thereof is 100 times by weight, preferably 50 times by weight, more preferably 30 times by weight with respect to the 3-aralkyloxypyrrolidine derivative (2).

A nonpolar solvent is not particularly limited, and may include a hydrocarbon solvent such as an aliphatic hydrocarbon solvent and an aromatic hydrocarbon solvent.

The aliphatic hydrocarbon solvent is not particularly limited, and may include an aliphatic hydrocarbon having 5 to 8 carbon atoms such as pentane, hexane, heptane, and methylcyclohexane. Among them, an aliphatic hydrocarbon having 6 or 7 carbon atoms, specifically, hexane, heptane, methylcyclohexane and the like are preferred.

The aromatic hydrocarbon solvent is not particularly limited, and it is preferably an aromatic hydrocarbon having 6 to 8 carbon atoms, specifically, for example, benzene, toluene, xylene and the like. Among them, an aromatic hydrocarbon having 7 or 8 carbon atoms, preferably toluene, xylene and the like are preferred.

When a nonpolar solvent is used, it can be mixed with a polar solvent before use, but as necessary, it can be suitably added after the crystallization is occurred by such methods as reaction crystallization, cooling crystallization and concentration crystallization. Preferred method is adding the nonpolar solvent after the crystallization is occurred.

A crystallization temperature is not particularly limited, and it is normally 100° C. or less, preferably 80° C. or less, more preferably 60° C. or less, even more preferably 40° C. or less, particularly preferably 30° C. or less. A lower limit is normally −20° C., preferably −10° C., more preferably 0° C.

Crystallization is preferably carried out under a strong stirring condition wherein a power requirement of impeller (agitator power) per unit volume is 0.1 kW/m³ or more, preferably 0.3 kW/m³ or more, more preferably 0.5 kW/m³ or more.

The crystal of the 3-aralkyloxypyrrolidine derivative (2) thus obtained can be collected using a common solid-liquid separation method such as centrifugation, pressure separation, and filtration under reduced pressure. The resultant crystal can be obtained as a dry crystal by, for example, drying under reduced pressure (vacuum drying) as necessary.

The crystal of a 3-benzyloxypyrrolidine derivative represented by following general formula (4) obtained by above step as the 3-aralkyloxypyrrolidine derivative (2) in which R is benzyl, is a novel crystal which is isolated in the present invention for the first time, and is very useful as a pharmaceutical intermediate for its easiness in handling:

[Chemical formula 18]

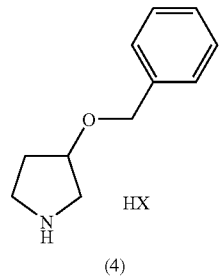

(4)

wherein R is benzyl. In the 3-benzyloxypyrrolidine derivative (4), HX is the same as above. The crystal of the 3-benzyloxypyrrolidine derivative (4) of the present invention may be a racemate or an optical active compound. In view of usefulness as a pharmaceutical intermediate, an optical active compound is preferred.

Needless to say, the crystal of the 3-aralkyloxypyrrolidine derivative (2) obtained by the present invention is a crystal with high purity. Namely, it has a chemical purity of 95% or more, preferably 97% or more, more preferably 98% or more, particularly 99% or more. Further, in a case of an optical active compound, the chemical purity thereof is preferably as the same as above, and optical purity is 98% ee or more, preferably 99% ee or more, more preferably 99.5% ee or more. Additionally, a content of the 3-hydroxypyrrolidine contained in the 3-aralkyloxypyrrolidine derivative (2) obtained by the crystallization step is normally 2% or less, preferably 1% or less, more preferably 0.5% or less, particularly preferably 0.3% or less. Further, impurities contained in the 3-aralkyloxypyrrolidine derivative (2) are normally 1% or less, preferably 0.5% or less, more preferably, 0.3% or less, particularly preferably 0.1% or less.

Next, a method for treating the 3-aralkyloxypyrrolidine hydrohalide (3) represented by a general formula (3) included in the 3-aralkyloxypyrrolidine derivative (2) is explained:

[Chemical formula 19]

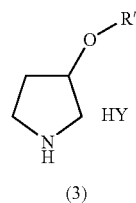

(3)

R' of the above formula (3) is an aralkyl group having 7 to 15 carbon atoms which may have a substituent or hydrogen atom. The aralkyl group having 7 to 15 carbon atoms which may have a substituent is same as the group explained as R of the above formula (1). Also, HY in the above formula (3) is hydrogen chloride, hydrogen bromide, hydrogen iodide, hydrogen fluoride, or a mixture thereof. It is preferably hydrogen chloride or hydrogen bromide, more preferably hydrogen chloride.

The 3-aralkyloxypyrrolidine hydrohalide (3) may be a racemate or an optical active compound. But an optical active compound is preferred.

The 3-aralkyloxypyrrolidine hydrohalide (3) can be produced by, for example, the process described in the 3-aralkyloxypyrrolidine derivative (2).

The method for handling of the present invention is particularly effective to the dry crystal of the 3-aralkyloxypyrrolidine hydrohalide (3). Here, the dry crystal means a crystal whose initial moisture content is less than an equilibrium moisture content under the environment and which absorbs moisture with time (i.e., moisture content increases). Preferred dry crystal is the one obtained by subjecting a crystal of the 3-aralkyloxypyrrolidine hydrohalide (3) to drying treatment such as drying under reduced pressure. The moisture content of the 3-aralkyloxypyrrolidine hydrohalide (3) is, although it depends on a type of handling operation and an operation time, for example, 3% by weight or less, preferably 2% by weight or less, more preferably 1% by weight or less, even more preferably 0.5% by weight or less, particularly preferably 0.3% by weight or less.

In order to solve the above described problems, the present invention is characterized by handling the crystal of the 3-aralkyloxypyrrolidine hydrohalide (3) under an environment of absolute humidity of 12 $g/m^3$ or less, preferably 10 $g/m^3$ or less, particularly preferably 8 $g/m^3$ or less. By handling under the above condition of humidity, absorption of moisture is suitably suppressed so that deliquescence of the 3-aralkyloxypyrrolidine hydrohalide (3) can be prevented.

In the present invention, the humidity of the environment is controlled by dehumidification from the environment, or an introduction of the dehumidified gas (preferably, a dry inactive gas such as dry nitrogen) to the environment and the like. For example, in order to accomplish the environment with an absolute humidity of 12 $g/m^3$ or less, an absolute humidity in a sealed box is 12 $g/m^3$ or less when handled in the box, or an ambient absolute humidity of the crystal of the 3-aralkyloxypyrrolidine hydrohalide (3) is measured when handled indoors; the measured point is not particularly limited, and for example, is within 1 to 30 m in the same indoor space. The method for measuring the absolute humidity may include direct measurement using a commercially available absolute hygrometer; another method is to measure each of a temperature and a relative humidity in the environment to calculate the absolute humidity from the product of a saturated water vapor concentration ($g/m^3$) and a relative humidity (%) at the temperature.

A method of dehumidification is not particularly limited, and is achieved by icing of moisture, and a use of dehumidifier or desiccant (silica gel and the like). Additionally, a particularly preferred method includes a method wherein a crystal of the 3-aralkyloxypyrrolidine hydrohalide (3) is handled in a low temperature environment. Namely, under a low temperature environment, a saturated water vapor concentration in an atmosphere is essentially lowered, so that even in a region with high humidity such as Japan, the environment of low humidity can be easily provided. In this manner, the absorption of moisture of the crystal of the 3-aralkyloxypyrrolidine hydrohalide (3) can be suitably suppressed, thereby preventing deliquescence thereof. The low temperature normally means 25° C. or less, preferably 20° C. or less, more preferably 10° C. or less, particularly 5° C. or less.

Therefore, according to the present invention, under an environment satisfying above absolute humidity and a particularly low temperature, a crystal of the 3-aralkyloxypyrrolidine hydrohalide (3) can be handled stably even on a large scale (industrial scale) while maintaining a high quality.

As described above, the 3-aralkyloxypyrrolidine hydrohalide (3) useful as an intermediate for pharmaceutical products and the like can be suitably handled on a large scale (industrial scale) by the present invention.

Needless to say, as long as an environment satisfying above absolute humidity is provided, a method for accomplishing it is not particularly limited. The present invention can be carried out under a normal pressure, under applied pressure, and under reduced pressure, and it can be carried out preferably under a normal pressure.

According to the method for handling, absorption of moisture of the crystal of the 3-aralkyloxypyrrolidine hydrohalide (3) is suppressed, so that even in a case of bringing in contact with a metal material, incorporation of the metal component into the solid as well as corrosion of the metal material is suppressed. On the other hand, under an environment with high humidity, absorption of moisture progresses to an extent that there occurs a harmful effect. Further, a metal component is considerably mixed in the solid and at the same time the metal material is considerably corroded. The metal material may be a stainless-steel, hastelloy, iron and the like. It may be, for example, SUS304, SUS304L, SUS316, SUS316L, SUS309S, SUS310S, SUS321 or SUS347 which is an austenite stainless-steel, particularly SUS304 or SUS316.

The metal component which can be mixed in the solid includes a transition metal such as iron, chromium, and nickel contained in stainless-steel or a salt of these. The metal components which are most likely to be mixed are iron, chromium, nickel, or a salt or a mixture of these, particularly iron or a salt thereof.

In the present invention, packaging and storing of the crystal of the 3-aralkyloxypyrrolidine hydrohalide (3) may be carried out, for example, by using one or more bag such as an aluminum laminated bag or a polyethylene bag, preferably by using an aluminum laminated bag as an outer bag and a polyethylene bag as an inner bag. Further, as necessary or preferably, a desiccant (such as silica gel) can be included. In a case of including a desiccant, it may be included in the inner bag, or may be packed inside the outer bag and outside the inner bag. The bag packed with a crystal may be, as necessary or preferably, put in an outer package such as a steel drum, a fiber drum, or a corrugated fiberboard.

An effect of the present invention can be maximized on a large scale (industrial scale). The scale is not particularly limited, and the crystal of the 3-aralkyloxypyrrolidine hydrohalide (3) is normally 1 kg or more, preferably 10 kg or more, more preferably 100 kg or more, particularly 1000 kg or more.

According to the present invention, even in a case where a handling time of the crystal of the 3-aralkyloxypyrrolidine hydrohalide (3) extends for a long period, the above described problems can be successfully solved by controlling a surrounding environment at an absolute humidity of 12 $g/m^3$ or less, preferably 10 $g/m^3$ or less, particularly preferably 8 $g/m^3$ or less to suppress the absorption of moisture up to an equilibrium moisture content thereof (namely, a moisture content thereof is controlled to 3% by weight or less, preferably 2% by weight or less, more preferably 1% by weight or less, even more preferably 0.5% by weight or less, particularly preferably 0.3% by weight or less).

Needless to say, the crystal of the 3-aralkyloxypyrrolidine hydrohalide (3) obtained by the present invention is from white to light brown with high purity. Namely, a chemical purity is preferably 95% or more, more preferably 96% or more, even more preferably 97% or more, still further preferably 98% or more, particularly 99% or more. Further, when the 3-aralkyloxypyrrolidine hydrohalide (3) is optical active, the chemical purity thereof is preferably as the same as above, and optical purity is 98% ee or more, preferably 99% ee or more, more preferably 99.5% ee or more, particularly preferably 99.8% ee or more.

EXAMPLES

Hereinafter, the present invention is described in more detail with reference to Examples, but the present invention is not restricted by the following Examples.

A content of the 3-hydroxypyrrolidine derivative, a content of the impurities and the optical purity described in Examples were analyzed by the following HPLC method.

[Analysis method for purity, content of impurities]
Column: Cosmosil 5C18ARII (250×4.6 mm; manufactured by Nacalai), Mobile phase: $KH_2PO_4$
buffer (pH3)/acetonitrile =80/20(v/v),
Flow rate: 0.5 ml/min (0 to 20 minutes), 1.5 ml/min (20 to 30 minutes),
Detection: UV 210nm,
Column temperature:
40° C.

[Analysis Method for Content of 3-Hydroxypyrrolidine]
In this analysis, 3-hydroxypyrrolidine hydrochloride was converted to tert-butoxycarbonylamino-3-hydroxypyrrolidine to be quantified.
(Derivation from 3-hydroxypyrrolidine hydrochloride)
After 3-benzyloxypyrrolidine hydrochloride containing 3-hydroxypyrrolidine hydrochloride was dissolved in isopropanol and neutralized with 30% aqueous solution of sodium hydroxide, di-tert-butyl dicarbonate was added and the mixture was subjected to ultrasound treatment. The resultant mixture was injected into HPLC for analysis.
(Analytical condition)
Column: AQ303 (250×4.6 mm, 5 μm; manufactured by YMC),
Mobile phase A: 0.5% $KH_2PO_4$ aqueous solution,
Mobile phase B: acetonitrile,
Flow rate: 1.0 ml/min,
Detection: UV 210 nm,
Column temperature: 40° C.
Gradient conditions:

| Time (minute) | Liquid A (%) | Liquid B (%) |
| --- | --- | --- |
| 0 | 80 | 20 |
| 10 | 40 | 60 |
| 30 | 40 | 60 |
| 31 | 80 | 20 |
| 40 | 80 | 20 |

Retention time: 10.4 minutes for N-tert-butoxycarbonylamino-3-hydroxypyrrolidine (Boc-protected 3-hydroxypyrrolidine), 24.1 minutes for N-tert-butoxy-carbonylamino-3-benzyloxypyrrolidine(Boc-protected 3-benzyloxypyrrolidine)

[Analysis Method for Determining Optical Purity]
In this analysis, 3-aralkyloxypyrrolidine is converted to tert-butoxycarbonylamino-3-benzyloxypyrrolidine to measure optical purity.
(Derivation from 3-Aralkyloxypyrrolidine Hydrochloride)
After 3-benzyloxypyrrolidine hydrochloride containing enantiomer was dissolved into isopropanol and neutralized with 30% aqueous solution of sodium hydroxide, di-tert-butyl dicarbonate was added and the mixture was subjected to ultrasound treatment. The resultant mixture was injected into HPLC for analysis.
(Analytical condition)
Column: CHIRALPAK AD-H (4.6 mm×250 mm; manufactured by Daicel),
Mobile phase: hexane/IPA=98/2(v/v),
Flow rate: 1.0 ml/min,
Detection: UV 210 nm,
Column temperature: 13° C.
Retention time: 13.4 minutes for (R)-N-tert-butoxycarbonylamino-3-benzyloxypyrrolidine(Boc-protected (R)-3-benzyloxypyrrolidine), 12.1 minutes for (S)-N-tert-butoxycarbonylamino-3-benzyloxypyrrolidine(Boc-protected (S)-3-benzyloxypyrrolidine)

Example 1

N-tert-butoxycarbonyl-(R)-3-hydroxypyrrolidine 124 g of (R)-3-hydroxypyrrolidine hydrochloride was dissolved in 187 g of distilled water and neutralized by adding 217 g of aqueous solution of potassium carbonate (containing 72 g of potassium carbonate). 431 g of THF solution of di-tert-butyl dicarbonate (containing 214 g of di-tert-butyl dicarbonate) was dropped into the solution. After stirring for a while, an extraction was carried out with 565 g of toluene, and the mixture was concentrated, thereby obtaining 180 g of N-tert-butoxycarbonyl-(R)-3-hydroxypyrrolidine (yield of 96%).
$^1$H-NMR (CDCl$_3$): δ(ppm) 1.48(s, 9H), 1.86-2.04(m, 3H), 3.26-3.56 (m, 4H), 4.45(m, 1H).

Example 2

N-tert-butoxycarbonyl-(R)-3-benzyloxypyrrolidine 180 g of N-tert-butoxycarbonyl-(R)-3-hydroxypyrrolidine was dissolved into 725 g of toluene, followed by adding 31 g of tetra-n-butyl ammonium bromide and 16 g of potassium iodide as a catalyst. Further, after 1924 g of 10% aqueous solution of sodium hydroxide was added and the mixture was heated to 50° C., 158 g of benzyl chloride was dropped. After the reaction finished, the mixture was cooled to 25° C. and an organic layer was washed with water. The resultant organic layer was concentrated, thereby obtaining 244 g of N-tert-butoxycarbonyl-(R)-3-benzyloxypyrrolidine (yield of 92%). A residual quantity of N-tert-butoxycarbonyl-(R)-3-hydroxypyrrolidine with respect to N-tert-butoxycarbonyl-(R)-3-benzyloxypyrrolidine was 1.1 wt %.
$^1$H-NMR (CDCl$_3$): δ(ppm) 1.46(s, 9H), 1.87-2.11 (m, 2H), 3.42-3.50(m, 4H), 4.13(m, 1H), 4.53(s, 2H), 7.26-7.39(m, 5H).

Example 3

N-tert-butoxycarbonyl-(R)-3-benzyloxypyrrolidine 74 g of N-tert-butoxycarbonyl-(R)-3-hydroxypyrrolidine separately obtained was dissolved in 296 g of toluene and then 6.4 g of tetra-n-butyl ammonium bromide was added. Further, after 264 g of 30% aqueous solution of sodium hydroxide was added and was heated to 72° C., 65 g of benzyl chloride was dropped. At the stage where remaining N-tertbutoxycarbonyl-(R)-3-hydroxypyrrolidine with respect to N-tert-butoxycarbonyl-(R)-3-benzyloxypyrrolidine became 1.3 wt %, a reaction temperature was cooled to 25° C. to stop the reaction. The resultant organic layer was washed with water and was concentrated, thereby obtaining 83 g of N-tert-butoxycarbonyl-(R)-3-benzyloxypyrrolidine (yield of 97%).

$^1$H-NMR (CDCl$_3$): δ(ppm) 1.46(s, 9H), 1.87-2.11(m, 2H), 3.42-3.50(m, 4H), 4.13(m, 1H), 4.53(s, 2H), 7.26-7.39(m, 5H).

Example 4

(R)-3-benzyloxypyrrolidine hydrochloride

After 101 g of N-tert-butoxycarbonyl-(R)-3-benzyloxypyrrolidine separately obtained was dissolved in 149 g of isopropanol and heated to 40° C., 138 g of isopropanol solution of hydrogen chloride was dropped for 6 hours. After the reaction finished, the mixture was cooled to 23° C. and was concentrated to distil the solvent away. Further, 1400 g of ethyl acetate was added and the mixture was concentrated, thereby obtaining a concentrate in an amount of about 300 g. Then, the concentrate was heated to 40° C., and isopropanol was added until (R)-3-benzyloxypyrrolidine hydrochloride which had been separated as an oily substance became completely dissolved. After (R)-3-benzyloxypyrrolidine hydrochloride was crystallized by gradually cooling the solution and suitably adding a seed crystal, 195 g of hexane was further added. At the time, crystallization solvent was in a following proportion: isopropanol/ethyl acetate/hexane=1/71.5/71.5. a deposited crystal was subjected to filtration under reduced pressure, and the resultant wet crystal was washed with 389 g of ethyl acetate, and then a wet crystal was dried under reduced pressure, thereby obtaining 64 g of dry crystal of (R)-3-benzyloxypyrrolidine hydrochloride (yield of 82%, purity of 99.8%). The content of (R)-3-hydroxypyrrolidine hydrochloride was reduced from 0.92 wt % to 0.42 wt % by this crystallization operation. Additionally, the content of benzyl alcohol was reduced from 1.9 wt % to 0.01 wt % by this crystallization operation.

$^1$H-NMR (D$_2$O): δ(ppm) 2.12-2.30(m, 2H), 3.34-3.54 (m, 4H), 4.48(m, 1H), 4.60(s, 2H), 7.40-7.48(m, 5H). Melting point: 70.4 to 71.5° C.

Example 5

(R)-3-benzyloxypyrrolidine hydrochloride

After 242 g of N-tert-butoxycarbonyl-(R)-3-benzyloxypyrrolidine obtained in Example 2 was dissolved in 360 g of isopropanol and the mixture was heated to 40° C., 254 g of isopropanol solution of hydrogen chloride was dropped for 6 hours. After the reaction finished, the mixture was cooled to 25° C. and was concentrated to distil the solvent away. Further, 3600 g of ethyl acetate was added and the mixture was concentrated, thereby obtaining about 900 g of a concentrate. Then, the concentrate was heated to 40° C., and isopropanol was added until (R)-3-benzyloxypyrrolidine hydrochloride which had been separated as an oily substance became completely dissolved. After (R)-3-benzyloxypyrrolidine hydrochloride was crystallized by gradually cooling the solution and suitably adding a seed crystal, 93 g of hexane was further added. At the time, crystallization solvent was in a following proportion: isopropanol/ethyl acetate/hexane=1/25/6.3. A deposited crystal was subjected to filtration under reduced pressure, and the resultant wet crystal was washed with 558 g of ethyl acetate, and then a wet crystal was dried under reduced pressure, thereby obtaining 146 g of dry crystal of (R)-3-benzyloxypyrrolidine hydrochloride (yield of 78%, purity of 99.2%). The content of (R)-3-hydroxypyrrolidine hydrochloride was reduced from 1.2 wt % to 0.3 wt % by this crystallization operation. Additionally, the content of the benzyl alcohol was reduced from 2.9 wt % to 0.05 wt % by this crystallization operation.

$^1$H-NMR (D$_2$O): δ(ppm) 2.12-2.30(m, 2H), 3.34-3.54(m, 4H), 4.48(m, 1H), 4.60(s, 2H), 7.40-7.48(m, 5H).

Comparative Example 1

(R)-3-benzyloxypyrrolidine hydrochloride

After 10 g of 1,4-dioxane solution obtained separately containing 6.6 g of (R)-3-benzyloxypyrrolidine hydrochloride was heated to 40° C., 170 g of toluene was added, and (R)-3-benzyloxypyrrolidine hydrochloride became oily.

Examples 6 to 8

Using a crude product of (R)-3-benzyloxypyrrolidine hydrochloride (purity of 98.4%) obtained separately, crystallization conditions other than those of the above Examples 4, 5 were examined, too. Operations and results are shown in Table 1.

[Testing Operation]

1.0 g of crude product of (R)-3-benzyloxypyrrolidine hydrochloride containing (R)-3-hydroxypyrrolidine hydrochloride (content of 0.13 wt %) and benzyl alcohol (content of 1.0 wt %) as impurities was dispersed in 4.0 g of various solvents. After the mixture was heated to 40° C., isopropanol was added thereto until the crude product was completely dissolved. The solution was gradually cooled to 24° C., and a seed crystal was added as necessary, thereby crystallizing. The deposited crystal was subjected to filtration under reduced pressure, and the resultant wet crystal was washed with 10 ml of ethyl acetate. Subsequently, the wet crystal was dried under a reduced pressure, thereby obtaining (R)-3-benzyloxypyrrolidine hydrochloride.

TABLE 1

| Example | Solvents | Amount of isopropanol added (mg) | Yield (%) | Purity (%) | Content of impurities (wt %) | |
|---|---|---|---|---|---|---|
| | | | | | (R)-3-hydroxypyrrolidine hydrochloride | Benzyl alcohol |
| 6 | Ethyl acetate | 250 | 83 | 99.8 | 0.01 or less | 0.01 or less |
| 7 | Tert-butyl acetate | 725 | 76 | 99.8 | 0.01 or less | 0.01 or less |
| 8 | Methyl tert-butyl ether | 900 | 85 | 100.0 | 0.01 or less | 0.01 or less |

Examples 9 to 14

Using a crude product of (R)-3-benzyloxypyrrolidine hydrochloride obtained separately (purity of 98.4%), crystallization conditions other than those of the Example 4 to 8 were examined, too. Operations and results are shown in Table 2.

[Testing Operation]

Into 1.0 g of crude product of (R)-3-benzyloxypyrrolidine hydrochloride containing (R)-3-hydroxypyrrolidine hydrochloride (content of 0.13 wt %) and benzyl alcohol (content of 1.0 wt %) as impurities, various solvents in an amount for complete dissolution at 40° C. was added. The solution was gradually cooled to about 22 to 24° C. (or to 3° C. in a case of acetone), and a seed crystal was added as necessary, thereby crystallizing. The deposited crystal was dried reduced pressure, and the resultant wet crystal was subjected to drying under reduced pressure, thereby obtaining a dry crystal of (R)-3-benzyloxypyrrolidine hydrochloride.

TABLE 2

| Example | Solvent | Amount of solvent added(g) | Yield (%) | Purity (%) | Content of impurities (wt %) (R)-3-hydroxypyrrolidine hydrochloride | Benzyl alcohol |
|---|---|---|---|---|---|---|
| 9 | Tetrahydrofuran | 4.0 | 20 | 99.9 | 0.01 or less | 0.01 or less |
| 10 | Chlorobenzene | 4.0 | 72 | 99.8 | 0.01 or less | 0.01 or less |
| 11 | Dichloroethane | 0.44 | 51 | 99.9 | 0.01 or less | 0.01 or less |
| 12 | Acetonitrile | 0.13 | 56 | 100.0 | 0.01 or less | 0.01 or less |
| 13 | Isopropanol | 0.22 | 45 | 100.0 | 0.01 or less | 0.01 or less |
| 14 | Acetone | 0.17 | 70 | 99.9 | 0.01 or less | 0.01 or less |

Example 15

(R)-3-benzyloxypyrrolidine

After 156 g of ethyl acetate and 100 g of water were added into 39 g of (R)-3-benzyloxypyrrolidine hydrochloride which had been obtained separately and the mixture was stirred for a while, an organic layer was separated. After 156 g of ethyl acetate was added to the resultant aqueous layer and cooled by ice, 24 g of 30% aqueous solution of sodium hydroxide was dropped. After stirring for a while and separating an aqueous layer, an organic layer was washed with 20 g of water. The resultant organic layer was concentrated and dried under reduced pressure, thereby obtaining 33 g (purity 86.6%) of a concentrate of (R)-3-benzyloxypyrrolidine. An amount of (R)-3-hydroxypyrrolidine with respect to (R)-3-benzyloxypyrrolidine was reduced from 0.84 wt % to 0.12 wt % by the above operations.

$^1$H-NMR (CDCl$_3$): δ(ppm) 1.85-1.92(m, 3H), 2.80-2.85 (m, 2H), 3.06-3.13(m, 2H), 4.10(m, 1H), 4.48(s, 2H), 7.24-7.34(m, 5H).

Example 16

(R)-3-benzyloxypyrrolidine hydrobromide 1.0 g of a concentrate containing (R)-3-benzyloxypyrrolidine obtained in Example 15 (purity of 86.6%) containing (R)-3-hydroxypyrrolidine (content of 0.12 wt %) and benzyl alcohol (content of 1.9 wt %) were contained as impurities were dissolved in 9 ml of isopropanol, followed by adding 0.82 g of 48% hydrobromic acid under ice cold condition. After stirring for a while, the mixture was concentrated and dried under reduced pressure, thereby obtaining a concentrate. After the concentrate was dispersed in 4.0 g of ethyl acetate and heated to 40° C. for complete dissolution, the solution was gradually cooled to 22° C. The deposited crystal was filtered under reduced pressure, and the resultant wet crystal was dried under reduced pressure, thereby obtaining 0.74 g of dry crystal of (R)-3-benzyloxypyrrolidine hydrobromide (yield of 59%, purity of 100.0%). Each of (R)-3-hydroxypyrrolidine and benzyl alcohol in the crystal was 0.01 wt % or less.

$^1$H-NMR(D$_2$O):δ(ppm)2.10-2.32(m,2H),3.34-3.54(m, 4H),4.49(m,1H),4.61(s,2H),7.41-7.48(m,5H).

Example 17

(R)-3-benzyloxypyrrolidine p-toluenesulfonate 1.0 g of a concentrate containing (R)-3-benzyloxypyrrolidine obtained in Example 15 (purity of 86.6%) containing (R)-3-hydroxypyrrolidine (content of 0.12 wt %) and benzyl alcohol (content of 1.9 wt %) as impurities were dissolved in 9 ml of isopropanol, followed by adding 0.93 g of p-toluenesulfonic acid monohydrate under ice cold conditions. After stirring for a while, the mixture was concentrated and dried under reduced pressure, thereby obtaining a white crystal. After the crude product was dispersed in 4.00 g of ethyl acetate and was heated to 40° C., 621 mg of isopropanol was added and the crude product was dissolved completely. The solution was gradually cooled to 22° C., and the deposited crystal was filtered under reduced pressure. The resultant wet crystal was washed with 10 ml of ethyl acetate, and then the wet crystal was dried under reduced pressure, thereby obtaining 1.15 g of dry crystal of (R)-3-benzyloxypyrrolidine p-toluenesulfonic acid (yield of 68%, purity of 100.0%). Each of (R)-3-hydroxypyrrolidine and benzyl alcohol in the crystal was 0.01 wt % or less.

$^1$H-NMR(D$_2$O):δ(ppm)2.06-2.30(m,2H),2.39(s,3H), 3.32-3.51(m,4H),4.46(m,1H),4.57(s,2H),7.36(d,J=7.8 Hz,2H),7.40-7.47(m,5H),7.69(d,J=8.3 Hz,2H).

Example 18

(R)-3-benzyloxypyrrolidine sulfate 1.0g of a concentrate containing (R)-3-benzyloxypyrrolidine obtained in Example 15 (purity of 86.6%) containing (R)-3-hydroxypyrrolidine(content of 0.12 wt %) and benzyl alcohol (content of 1.9 wt %) as impurities was dissolved in 9 ml of isopropanol, followed by adding 240 mg of sulfuric acid under ice cold conditions. After stirring for a while, the mixture was concentrated and dried under reduced pressure, thereby obtaining a concentrate. After the concentrate was dispersed in 4.0 g of ethyl acetate and was heated to 40° C., 209 mg of isopropanol was added and the concentrate was dissolved completely. After the solution was gradually cooled to 22° C., 207 mg of hexane was added, and then a seed crystal was further added, and the deposited crystal was filtered under reduced pressure. The resultant wet crystal was dried under reduced pressure, thereby obtaining 75 mg of dry crystal of (R)-3-benzyloxypyrrolidine sulfate (yield of 7%, purity of 99.9%). Each of (R)-3-hydroxypyrrolidine and benzyl alcohol in the crystal was 0.01 wt % or less.

$^1$H-NMR(D$_2$O):δ(ppm)2.10-2.32(m,2H),3.34-3.54(m, 4H),4.49(m,1H),4.61(s,2H),7.39-7.48(m,5H).

Example 19

(R)-3-benzyloxypyrrolidine benzoate 1.0 g of a concentrate of (R)-3-benzyloxypyrrolidine obtained in Example 15 (purity of 86.6%) containing (R)-3-hydroxypyrrolidine (content of 0.12 wt %) and benzyl alcohol (content of 1.9 wt %) as impurities was dissolved in 9 ml of isopropanol followed by adding 0.60 g of benzoic acid. After stirring for a while, the mixture was concentrated and dried under reduced pressure, thereby obtaining a white crystal. The crude product was dispersed in 4.0 g of ethyl acetate and was heated to 40° C., and 1.19 g of isopropanol was added and the crude product was completely dissolved. After the solution was gradually cooled to 22° C., the deposited crystal was filtered under reduced pressure. The resultant wet crystal was washed with 10 ml of ethyl acetate, and then the wet crystal was dried under reduced pressure, thereby obtaining 0.69 g of dry crystal of (R)-3-benzyloxypyrrolidine benzoate (yield of 47%, purity of 100.0%). Each of (R)-3-hydroxypyrrolidine and benzyl alcohol in the crystal was 0.01 wt % or less.

$^1$H-NMR(D$_2$O):δ(ppm)2.08-2.32(m,2H),3.33-3.52(m, 4H),4.47(m,1H),4.58(s,2H),7.41-7.55(m,8H),7.87(d,J=7.8 Hz,2H).

Example 20

(R)-3-benzyloxypyrrolidine-(L)-tartrate 0.25g of a concentrate containing (R)-3-benzyloxypyrrolidine obtained separately (purity of 86.6%, optical purity of 97.0% ee) containing (R)-3-hydroxypyrrolidine (content of 0.12 wt %) and benzyl alcohol (content of 1.0 wt %) as impurities was dissolved in 40 ml of isopropanol, followed by adding 0.18 g of (L)-tartaric acid. After stirring for a while, the mixture was concentrated and dried under reduced pressure, thereby obtaining a white crystal. After the crude product was dispersed in 4.0 g of isopropanol and heated to 40° C., 400 mg of distilled water was added and the crude product was completely dissolved. The solution was gradually cooled to 22° C., and the deposited crystal was filtered under reduced pressure. The resultant wet crystal was washed with 10 ml of ethyl acetate, and then the wet crystal was dried under reduced pressure, thereby obtaining 0.16 g of dry crystal of (R)-3-benzyloxypyrrolidine-(L)-tartrate (yield of 52%, purity of 100.0%, optical purity of 98.2% ee). Each of (R)-3-hydroxypyrrolidine and benzyl alcohol in the crystal was 0.01 wt % or less.

$^1$H-NMR(D$_2$O):δ(ppm)2.08-2.32(m,2H),3.32-3 .54(m, 4H),4.31(d,J=3.2 Hz,1H),4.49(m,1H),4.61(s,2H),7.40-7.48 (m,5H).

Example 21

(R)-3-benzyloxypyrrolidine-(D)-tartrate 0.25g of a concentrate of (R)-3-benzyloxypyrrolidine obtained separately (purity of 86.6%, optical purity of 97.0% ee) containing (R)-3-hydroxypyrrolidine (content of 0.12 wt %) and benzyl alcohol (content of 1.0 wt %) as impurities was dissolved in 40 ml of isopropanol, and 183 mg of (D)-tartaric acid was added. After stirring for a while, the mixture was concentrated and dried under reduced pressure, thereby obtaining a white crystal. The crude product was dispersed in 4.0 g of isopropanol and was heated to 40° C., and 400 mg of distilled water was added and the crude product was completely dissolved. The solution was gradually cooled to 22° C., and the deposited crystal was filtered under reduced pressure. The resultant wet crystal was washed with 10 ml of ethyl acetate, and then the wet crystal was dried under reduced pressure, thereby obtaining 93 mg of dry crystal of (R)-3-benzyloxypyrrolidine-(D)-tartrate (yield of 30%, purity of 100.0%, optical purity of 97.5% ee). Each of (R)-3-hydroxypyrrolidine and benzyl alcohol in the crystal was 0.01 wt % or less.

$^1$H-NMR(D$_2$O):δ(ppm)2.08-2.32(m,2H),3.34-3.54(m, 4H),4.32(d,J=3.2 Hz,1H),4.49(m,1H),4.61(s,2H),7.40-7.48 (m,5H).

Example 22

(R)-3-benzyloxypyrrolidine-(L)-aspartate 0.25 g of a concentrate of (R)-3-benzyloxypyrrolidine obtained separately (purity of 86.6%, optical purity of 97.0% ee) containing (R)-3-hydroxypyrrolidine (content of 0.12 wt %) and benzyl alcohol (content of 1.0 wt %) as impurities was dissolved in 10 ml of distilled water, and 0.33 g of (L)-asparagic acid was added. After stirring for a while, isopropanol was added and the mixture was subjected to azeotropic dehydration, followed by concentration and drying under reduced pressure, thereby obtaining a white crystal. The crude product was dispersed in 4.0 g of isopropanol, and was heated to 40° C., and 506 mg of distilled water was added and the crude product was dissolved completely. The solution was gradually cooled to 22° C., and the deposited crystal was filtered under reduced pressure. The resultant wet crystal was washed with 10 ml of ethyl acetate and then the wet crystal was dried under reduced pressure, thereby obtaining 0.37 g of dry crystal of (R)-3-benzyloxypyrrolidine-(L)-aspartate (yield of 49%, purity of 100.0%, optical purity of 99.4% ee). A content of each of (R)-3-hydroxypyrrolidine and benzyl alcohol in the crystal was 0.01 wt % or less.

$^1$H-NMR(D$_2$O):δ(ppm)2.08-2.34(m,2H),2.67(dd,J=8.9 Hz,17.4 Hz,1H),2.82(dd,J=3.7 Hz,17.4 Hz,1H),3.34-3.54(m, 4H),3.89(dd,J=3.7 Hz,8.9 Hz,1H),4.49(m,1H),4.61(s,2H), 7.40-7.48(m,5H).

Example 23

(R)-3-benzyloxypyrrolidine-(D)-aspartate 0.25 g of a concentrate of (R)-3-benzyloxypyrrolidine obtained separately (purity of 86.6%, optical purity of 97.0% ee) containing (R)-3-hydroxypyrrolidine (content of 0.12 wt %) and benzyl alcohol (content of 1.0 wt %) as impurities was dissolved in 10 ml of distilled water, and 325 mg of (D)-asparagic acid was added. After stirring for a while, isopropanol was added and the solution was subjected to azeotropic dehydration, followed by concentration and drying under reduced pressure, thereby obtaining a white crystal. After the crude product was dispersed in 4.00 g of isopropanol and was heated to 40° C., 466 mg of distilled water was added and the crude product was dissolved completely. The solution was gradually cooled to 22° C., and the deposited crystal was filtered under reduced pressure. The resultant wet crystal was washed with 10 ml of ethyl acetate and then the wet crystal was dried under reduced pressure, thereby obtaining 0.17 g of dry crystal of (R)-3-benzyloxypyrrolidine-(D)-aspartate (yield of 22%, purity of 98.7%, optical purity of 99.8% ee). Each of (R)-3-hydroxypyrrolidine and benzyl alcohol in the crystal was 0.01 wt % or less.

$^1$H-NMR(D$_2$O):δ(ppm)2.08-2.34(m,2H),2.67(dd,J=8.9 Hz,17.4 Hz,1H),2.82(dd,J=3.7 Hz,17.4 Hz,1H),3.34-3.54(m, 4H),3.89(dd,J=3.7 Hz,8.9 Hz,1H),4.49(m,1H),4.61(s,2H), 7.40-7.48(m,5H).

Example 24

Measurement of absorption of moisture was carried out using (R)-3-benzyloxypyrrolidine hydrochloride obtained separately. Operations and results are shown in Table 3. The relative humidity was measured using a thermohygrometer manufactured by Isuzu Seisakusho Co., Ltd.

[Testing Operation]

(R)-3-benzyloxypyrrolidine hydrochloride (purity of 99.2%, moisture content of 0.25 wt %) was put in a container, and was left still in the container at a constant humidity (relative humidity of 22%, 33%, or 80% (25° C.)) in an open state. A moisture content of (R)-3-benzyloxypyrrolidine hydrochloride after being left still was measured using Karl Fischer Moisture Titrator.

The environment of each humidity was adjusted by placing each solution at the bottom of the desiccator at 25° C. Absolute humidity of 5 g/m$^3$: aqueous solution of saturated potassium acetate (relative humidity of 22%, 25° C.) Absolute humidity of 8 g/m$^3$: aqueous solution of saturated magnesium chloride (relative humidity 33%, 25° C.) Absolute humidity of 18 g/m$^3$: aqueous solution of saturated sodium chloride (relative humidity of 80%, 25° C.)

TABLE 3

| Absolute humidity of 5 g/m$^3$ | | Absolute humidity of 8 g/m$^3$ | | Absolute humidity of 18 g/m$^3$ | |
|---|---|---|---|---|---|
| Time of leaving still (hours) | Moisture content (wt %) | Time of leaving still (hours) | Moisture content (wt %) | Time of leaving still (hours) | Moisture content (wt %) |
| 0 | 0.25 | 0 | 0.25 | 0 | 0.25 |
| 1 | 0.46 | 1 | 0.56 | 1 | Deliquescence |
| 24 | 0.44 | 24 | 2.02 | | |

Example 25

N-tert-butoxycarbonyl-(R)-3-benzyloxypyrrolidine 187 mg of N-tert-butoxycarbonyl-(R)-3-hydroxypyrrolidine prepared separately was dissolved in 748 mg of toluene followed by adding 16 mg of tetra-n-butyl ammonium bromide and 9 mg of sodium iodide. Further, after 666 mg of 30% aqueous solution of sodium hydroxide was added and the mixture was heated to 50° C., 164 mg of benzyl chloride was dropped. A reaction temperature was cooled to 25° C. to stop the reaction at the stage where a remaining N-tert-butoxycarbonyl-(R)-3-hydroxypyrrolidine became 6.4 wt % with respect to N-tert-butoxycarbonyl-(R)-3-benzyloxypyrrolidine.

Example 26

N-tert-butoxycarbonyl-(R)-3-benzyloxypyrrolidine

Dimethyl sulfoxide (50 g) was added to about 60% toluene solution of N-tert-butoxycarbonyl-(R)-3-hydroxypyrrolidine (20 g) which had been obtained separately, and potassium iodide (5.32 g) and a solid of 85% potassium hydroxide (14.1 g) were added thereto. After the slurry solution was heated to 70° C., benzyl chloride (17.58 g) was dropped for 5 hours. Subsequently, after the solution was stirred for 16 hours, a conversion rate (*) reached 98%. After the reaction finished, the solution was cooled to 20° C., and toluene and 30% aqueous solution of sodium thiosulfate were added and an aqueous layer was removed, followed by washing an organic layer with water. The resultant organic layer was concentrated under reduced pressure, thereby obtaining toluene solution of N-tert-butoxycarbonyl-(R)-3-benzyloxypyrrolidine (yield: 98%).

(*) Conversion rate (%)=(amount of production of N-tert-butoxycarbonyl-(R)-3-benzyloxypyrrolidine(g))/[amount of production of N-tert-butoxycarbonyl-(R)-3-benzyloxypyrrolidine(g))+(residual amount of N-tert-butoxycarbonyl-(R)-3-hydroxypyrrolidine (g))]

Examples 27 to 28

A similar reaction operation was carried out except that toluene and dimethyl sulfoxide which were solvents of Example 26 were replaced by a single solvent described below and that a reaction temperature and a reaction time were changed. Results are shown in Table 4.

TABLE 4

| Example | Solvent | Temperature | Reaction time | Conversion rate |
|---|---|---|---|---|
| 27 | Acetonitrile | 70° C. | 42 hours | 93% |
| 28 | Toluene | 80° C. | 72 hours | 98% |

The invention claimed is:

1. A process for producing a crystallized 3-aralkyloxypyrrolidine derivative (2) comprising subjecting a non-crystallized 3-aralkyloxypyrrolidine derivative (2) to a crystallization process using a solvent comprising a polar organic solvent to obtain the crystallized 3-aralkyloxypyrrolidine derivative (2), wherein the 3-aralkyloxypyrrolidine derivative (2) is represented by the following formula (2):

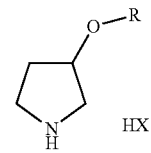

wherein R represents a benzyl group; and HX represents a mineral acid, sulfonic acid, carboxylic acid or amino acid.

2. The process according to claim 1, wherein the polar organic solvent is an ester solvent and/or an alcohol solvent.

3. The process according to claim 1, wherein the crystallization process comprises adding a seed crystal.

4. The process according to claim 1, further comprising, before the crystallization process, purifying the non-crystallized 3-aralkyloxypyrrolidine derivative (2) by a series of operations of:

A) treating an aqueous layer with a base after removing an organic layer from a two-phase mixture of water and an organic solvent containing a 3-aralkyloxypyrrolidine derivative (2);

B) extracting a free amine of the 3-aralkyloxypyrrolidine derivative (2) using an organic solvent; and C) treating the free amine with an acid to convert the 3-aralkyloxypyrrolidine derivative (2) to the non-crystallized 3-aralkyloxypyrrolidine derivative (2).

5. The process according to claim 1 or 4, wherein the non-crystallized 3-aralkyloxypyrrolidine derivative (2) is obtained by removing a N-protecting group of a N-protected-3-aralkyloxypyrrolidine (1) represented by formula (1);

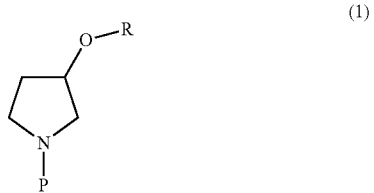
(1)

wherein R represents a benzyl group; and P represents a protecting group of an amino group.

6. The process according to claim 5, wherein the N-protected-3-aralkyloxypyrrolidine (1) is obtained by O-aralkylation of a hydroxyl group of N-protected-3-hydroxypyrrolidine represented by formula (5);

(5)

wherein P represents a protecting group of an amino group.

7. The process according to claim 1 or 4, wherein the non-crystallized 3-aralkyloxypyrrolidine derivative (2) is optically active.

8. The process according to claim 5, wherein the N-protected-3-aralkyloxypyrrolidine (1) is one obtained by O-aralkylation of a N-protected-3-hydroxypyrrolidine represented by formula (5) by allowing an aralkyl halide to act in the presence of a base and at least one of a metal halide and a phase-transfer catalyst:

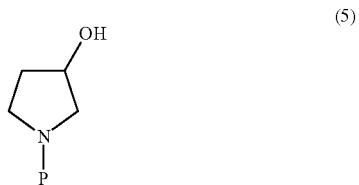
(5)

wherein P represents a protecting group of an amino group.

9. The process according to claim 6, wherein the pyrrolidine derivatives represented by the above formula (1) and (5) are optically active.

10. The process according to claim 1, wherein the crystallized 3-aralkyloxypyrrolidine derivative (2) is optically active, and/or the non-crystallized 3-aralkyloxypyrrolidine derivative (2) is optically active.

* * * * *